United States Patent
Breuer et al.

[11] 3,989,696
[45] Nov. 2, 1976

[54] 3-HETEROTHIO[(OXYALKYL)THIOACETYL]CEPHALOSPORIN DERIVATIVES

[75] Inventors: Hermann Breuer; Uwe D. Treuner, both of Regensburg, Germany

[73] Assignee: E. R. Squibb & Sons, Inc., Princeton, N.J.

[22] Filed: May 1, 1975

[21] Appl. No.: 573,677

[52] U.S. Cl. ............................. 260/243 C; 424/246
[51] Int. Cl.² ............... C07D 501/50; C07D 501/54
[58] Field of Search ................................ 260/243 C

[56] References Cited
FOREIGN PATENTS OR APPLICATIONS
2,304,226   8/1973   Germany.......................... 260/243 C OTHER PUBLICATIONS
Sassiver et al., Antimicrobial Agents & Chemotherapy 1968, pp. 101–108 (1969).

Primary Examiner—Nicholas S. Rizzo
Assistant Examiner—Diana G. Rivers
Attorney, Agent, or Firm—Lawrence S. Levinson; Merle J. Smith

[57] ABSTRACT

3-Heterothio[(oxyalkyl)thioacetyl] cephalosporin derivatives which have the formula

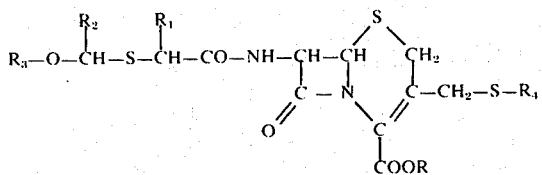

wherein R is hydrogen, lower alkyl, phenyl-lower alkyl, tri (lower alkyl) silyl, a salt forming ion, or the group

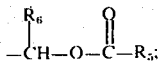

$R_1$ is hydrogen, lower alkyl, phenyl, thienyl or furyl; $R_2$ and $R_6$ each is hydrogen or lower alkyl; $R_3$ and $R_5$ is lower alkyl, phenyl or phenyl-lower alkyl; and $R_4$ is a five- or six-member nitrogen and/or sulfur or oxygen-containing ring system; are useful as antibacterial agents.

16 Claims, No Drawings

3-HETEROTHIO[(OXYALKYL)THIOACETYL]-CEPHALOSPORIN DERIVATIVES

SUMMARY OF THE INVENTION

This invention relates to new [(oxyalkyl)thioacetyl] cephalosporin derivatives of the formula

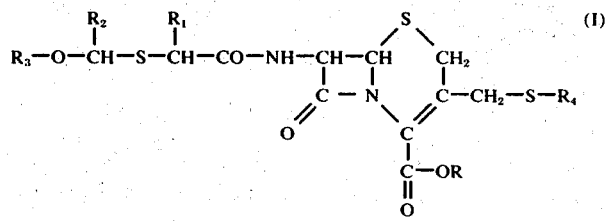

R represents hydrogen, lower alkyl, phenyl-lower alkyl, tri (lower alkyl)silyl, a salt forming ion or the group

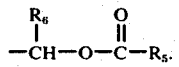

$R_1$ represents hydrogen, lower alkyl, phenyl, thienyl or furyl.

$R_2$ and $R_6$ each represents hydrogen or lower alkyl.

$R_3$ and $R_5$ each represents lower alkyl, phenyl or phenyl-lower alkyl.

$R_4$ is a five-membered or six-membered nitrogen or nitrogen and sulfur or oxygen-containing heterocyclic group including oxadiazole, triazole, thiatriazole, tetrazole, 1-oxopyridine and their lower alkyl substituted analogs, particularly the heterocyclics having the structures wherein $R_7$ represents hydrogen or lower alkyl.

DETAILED DESCRIPTION OF THE INVENTION

The various groups represented by the symbols have the meaning defined below and these definitions are retained throughout this specification.

The lower alkyl groups are straight or branched chain hydrocarbon groups containing 1 to 8 carbon atoms, preferably 1 to 4 carbons. Examples of the type of these groups are methyl, ethyl, propyl, isopropyl, butyl, t-butyl, pentyl, isopentyl, etc. The phenyl-lower alkyl groups include such lower alkyl groups attached to a phenyl (or two phenyl groups), e.g., benzyl, phenethyl, diphenylmethyl, etc.

The salt forming ions represented by R are metal ions, e.g., alkali metal ions such as sodium or potassium, alkaline earth metal ions such as calcium or magnesium, or an amine salt ion, of which a number are known for this purpose, for example, lower alkylamines like methylamine or triethylamine, aralkylamines like dibenzylamine, N,N-dibenzylethylenediamine, N-ethylpiperidine, etc.

Preferred embodiments of this invention are as follows:

R is hydrogen, alkali metal, diphenylmethyl, or

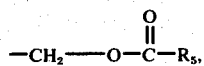

especially hydrogen, pivaloyloxymethyl, sodium or potassium. $R_5$ is lower alkyl, especially t-butyl.

$R_1$ is hydrogen, lower alkyl, especially 1 to 4 carbon alkyl, phenyl, especially hydrogen and phenyl.

$R_2$ and $R_6$ each is hydrogen or lower alkyl, preferably 1 to 4 carbon alkyl, especially hydrogen.

$R_3$ is lower alkyl, especially methyl.

$R_4$ is thiadiazole, tetrazole and their methyl substituted analogs, especially 1,3,4-thiadiazole, 5-methyl-1,3,4-thiadiazole, tetrazole and 1-methyltetrazole.

The new derivatives of [(oxyalkyl)thioacetyl]-cephalosporins of this invention are produced by reacting 7-aminocephalosporanic acid (7-ACA) (or derivatives wherein $R_3$ is other than hydrogen) with a mercaptan HS-$R_4$ at a pH of about 8 – 8.5 to obtain the derivative of the formula (II)

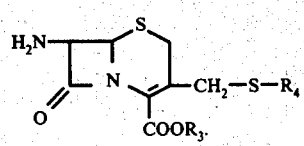

The product of formula II is then acylated on the amino group with an [(oxyalkyl)thio]acetic acid of the formula

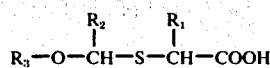

or an activated derivative like acid chloride, mixed anhydride or activated ester.

According to a preferred modification, the 7-aminocephalosporanic acid derivative of formula II, preferably an ester like the diphenylmethyl ester, and the acid of formula III are dissolved in an organic solvent like tetrahydrofuran or methylene chloride, then dicyclohexylcarbodiimide, or other coupling reagent, in an organic solvent like the one mentioned above, is added at a reduced temperature of about 0°–5° C. The dicyclohexylurea formed during the reaction is removed and the product is recovered from the filtrate. The diphenylmethyl group is removed, for example, by treatment with trifluoroacetic acid and anisole.

According to another modification, the [(oxyalkyl)thio]acetic acid is converted to the acid chloride with an agent such as oxalyl chloride or thionyl chloride and the acid chloride, in an oganic solvent like acetone, is added at a low temperature, e.g., 0° C. or below, to a mixture of the 7-aminocephalosporanic acid derivative of formula II, and a salt forming organic base, such a triethylamine, pyridine or the like, in an inert organic solvent such as acetone, chloroform, methylene chloride, dioxane, benzene or the like. The product of the reaction is then isolated by conventional procedures, e.g., by concentration, solvent extraction or evaporation of the solvent.

Alternatively, 7-ACA or a derivative thereof ($R_3$ in formula II is other than hydrogen), can be first acylated as described in our copending application serial no. 573,676, filed simultaneously herewith, then the product of this reaction is made to react with the mercaptan HS-$R_4$ at an alkaline pH, e.g., about pH 7.8.

Any of the salts can be produced from the free acid by conventional treatment, e.g., with potassium ethyl hexanoate, sodium bicarbonate or the like.

When R is the acyloxymethyl group

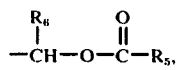

this group can be introduced into the 7-aminocephalosporanic acid moiety prior to the reaction with the [(oxyalkyl)thio] acetic acid or derivative by treatment with one to two moles of a halomethyl ester of the formula

wherein hal is halogen, preferably chlorine or bromine, in an inert organic solvent such as dimethylformamide, acetone, dioxane, benzene, or the like, at about ambient temperature or below.

The [(oxyalkyl)thio]acetic acid of formula III is produced by reacting a mercaptoacetic acid of the formula

with a halogenated compound of the formula

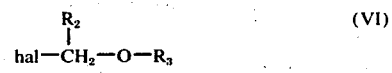

in the presence of a base like triethylamine in a solvent like tetrahydrofuran and then hydrolyzing the ester formed in the process.

Alternatively, when the acid halide is used to react with the 7-aminocephalosporanic acid compound, an alkoxide $R_3$-OMe (wherein Me is a metal like potassium) is made to react with a haloester of the formula

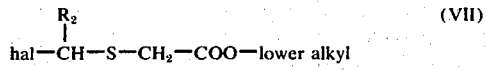

to obtain the intermediate of the formula

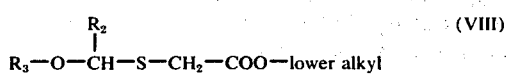

Treatment with a base, e.g., an alkali metal hydroxide, converts the ester to a salt which is then converted to the acid chloride with a halogenating agent like oxalyl chloride.

Further process details are also provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They can be used as antibacterial agents to combat infections due to organisms such as those named above, and in general may be utilized in a manner similar to cephradine and other cephalosporins. For example, a compound of formula I or a physiologically acceptable salt thereof can be used in various animal species in an amount of about 2 to 100 mg./kg., daily, orally or parenterally, in single or two to four divided doses to treat infections of bacterial origin, for example, 5.0 mg./kg. is used in mice.

Up to about 600 mg. of a compound of formula I or a physiologically acceptable salt thereof is incorporated in an oral dosage from such as tablets, capsules or elixirs or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

154.6 g. (1 mol.) of [(chloromethyl)thio] acetic acid methyl ester are dissolved in 1000 ml. of absolute methanol, cooled to −30° and, at this temperature, 500 ml. of a 2N sodium methoxide solution is added dropwise. The reaction mixture is stirred for 3 more hours at 0° and 10 g. of glacial acetic acid are added. The precipitate is filtered off under suction and the filtrate is concentrated. 1 liter of ether is added to the residue and additional precipitate is filtered off. The solvent is evaporated off and the residue is fractionated under vacuum. After distilling twice, the yield of [(methoxymethyl)thio]acetic acid methyl ester is 30.3 g., b.p. 85°–90° (10 mm.).

EXAMPLE 2

2.4 g. (0,016 mol.) [methoxymethyl)thio] acetic acid methyl ester are dissolved in 20 ml of isopropanol and 10 ml. of a 2N solution of potassium hydroxide in methanol are added. The reaction mixture is let stand for two hours at room temperature and one hour in the refrigerator, then the crystalline [(methoxymethyl)thio] acetic acid potassium salt which has formed is filtered under suction, yield 2.0 g., m.p. >250°.

EXAMPLE 3

8.7 g. (0.05 mol.) of [(methoxymethyl)thio]acetic acid potassium salt are finely divided and suspended in 50 ml. of methylene chloride. 0.1 ml. of pyridine is added and then a solution of 12.6 g. (0.1 mol.) of oxalyl chloride in 16 ml. of methylene chloride are added dropwise at room temperature with stirring. The mixture is stirred for an additional three hours. This is then concentrated, absolute ether is added to the residue, the filtrate is again concentrated and the oily residue,

[(methoxymethyl)thio] acetyl chloride, is distilled in vacuo yield 3.6 g. b.p. 40–42° (0.05 mm.).

EXAMPLE 4

16.8 g. (0.1 mol.) of α-mercaptobenzeneacetic acid are dissolved in 100 ml. of anhydrous tetrahydrofuran and 24 g. (0.3 mol.) of chloroacetone are added. This is cooled to 0° and 41.4 ml. of triethylamine are added dropwise under nitrogen. The mixture is stirred overnight at room temperature, then washed with water, sodium bicarbonate solution and more water. The solution is dried with magnesium sulfate, the solvent is evaporated and the residue is distilled in vacuo. The yield of 2-[(methoxymethyl)thio]benzeneacetic acid methoxymethyl ester is 16.7 g., b.p. 132°–135°.

EXAMPLE 5

2.56 g.(0.01 mol.) of α-[(methoxymethyl)thio] benzeneacetic acid methoxymethyl ester are dissolved in 10 ml. of methanol and 10 ml. of 2N methanolic potassium hydroxide solution are added. The reaction mixture is let stand overnight. The solvent is evaporated and water is added to the solid residue. This is extracted once with ether. The aqueous phase is acidified and the oil which separates is taken up in ether. The ether extract is washed with water and dried with magnesium sulfate. After evaporating the solvent, 2.1 g. of α-](methoxymethyl)thio] benzeneacetic acid remains as an oily residue.

EXAMPLE 6

A mixture of 13.6 g. (0.5M) of 7-aminocephalosporanic acid (7-ACA) in 100 ml. of water and 50 ml. of acetone are brought to pH 8 with sodium hydroxide while stirring. 9.8 g. (0.57M) of 2-methyl-1,3,4-thiadiazole-5-thiol are added and the mixture is heated at 80° for 4 hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl) thio]-methyl]-7-amino-8-oxo-5-thia-1-azabicyclo [4.2.0]-oct-2-ene-2-carboxylic acid is purified by dissolving in sodium bicarbonate solution and reprecipitating with 2N hydrochloric acid; yield 12.7 g., m.p. 206°.

EXAMPLE 7

By substituting 3-methyl-1,2,4-thiadiazole-5-thiol for the 2-methyl-1,3,4-thiadiazole-5-thiol in the procedure of Example 6,11.6 g. of 3-[[(3-methyl-1,2,4-thiadiazol-5-yl)thio]methyl]-7-amino-8-oxo-5-thia-1-azabicyclo [4.2.0]oct-2-ene-2-carboxylic acid, m.p. 186° (dec.) are obtained.

EXAMPLE 8

By substituting 0.57M of 1-methyl-1H-tetrazole-5-thiol for the 2-methyl-1,3,4-thiadiazole-5-thiol in the procedure of Example 6, 3-[[(1-methyl-1H-tetrazol-5-yl)thio]methyl]-7-amino-8-oxo-5-thia-1-azabicyclo [4.2.0]oct-2-ene-2-carboxylic acid is obtained.

EXAMPLE 9

18 g. of 7-amino-3-[[(5-methyl-1,3,4-thiadiazol-5-yl)thio]methyl]-8-oxo-5-thia-1-azabicyclo[4.2.0]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. After 3 hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain the 10 g. of the product, 7-amino-3-[[(5-methyl-1,3,4-thiadiazol-2-yl)thio]methyl]-8-oxo-5-thia- 1-azabicyclo[4.2.0]oct-2-ene-2-carboxylic acid, diphenylmethyl ester, as a light brown powder, m.p.157°–159°. The product is recrystallized from tetrahydrofuran/petroleum ether. 7-Amino-3-[[(3-methyl-1,2,4-thiadiazol-5-yl)thio]methyl]-7-amino-8-oxo-5-thia-1-azabicyclo[4.2.0]oct-2-ene-2-carboxylic acid diphenylmethyl ester is similarly obtained by substituting the product of Example 7 as starting in aterial.

EXAMPLE 10

7-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester The product, 7-amino-3-[[(1-methyl-1H-tetrazol-5-yl)thio]methyl]-8-oxo-5-thia-1-azabicyclo[4.2.0]oct-2-enecarboxylic acid, diphenylmethyl ester, m.p. 168°–169° (dec.), is obtained by the procedure of Example 9 utilizing as starting material 7-amino-3[[(1-methyl-1H-tetrazol-5-yl)thio]-methyl]-8-oxo-5-thia-1-azabicyclo[4.2.0]oct-2-ene-2-carboxylic acid.

EXAMPLE 11

4.26 g. (0.013 mol.) of 7-amino-3-[[(1-methyl-1H-tetrazol-5-yl)thio]methyl]-8-oxo-5-thia-1-azabicyclo [4.2.0] oct-2-ene-2-carboxylic acid are suspended in a mixture of 40 ml. of acetone and 40 ml. of water and brought into solution by the addition of 1.9 ml. of triethylamine. This is cooled to 0°–5° and a solution of 2.6 g. (0.017 mol.) of [(methyoxymethyl)thio] acetyl chloride in 13 ml. of acetone is added dropwise with stirring. By the simultaneous addition of triethylamine, dissolved in a little acetone, the pH of the solution is held at about 7.5. The solution is stirred for 30 minutes more, ethyl acetate and water are added and it is acidified to pH2 with 2N hydrochloric acid. A sizeable precipitate is filtered off. The ethyl acetate phase is washed once with water, dried with magnesium sulfate and concentrated. The residual syrup solidifies on the addition of petroleum ether. 2.1 g. of 7β-[[[(methoxymethyl)-thio]acetyl]amino]-3-[[(1-methyl-1H-tetrazol-5-yl)thio]methyl]-8-oxo-5-thia-1-azabicyclo[4.2.0]oct-2-ene-2-carboxylic acid are obtained, m.p. 75°–80° (dec.).

EXAMPLE 12

1.95 g. of (0.0043 mol.) of the product of Example 11 are dissolved in 20 ml. of methanol and a solution of 0.361 g. (0.0043 mol.) of sodium bicarbonate in 10 ml. of water is added. This is stirred for 20 minutes and the methanol evaporated. The residual aqueous solution is diluted slightly, filtered and freeze dried. 1.9 g. of 7β-[[[(methoxymethyl)-thio]acetyl]amino]-3-[[(1-methyl-1H-tetrazol-5-yl)thio]-methyl]-8-oxo-5-thia-1- azabicyclo[4.2.0]oct-2-ene-2-carboxylic acid sodium salt are obtained, m.p. 115°–126° (dec.).

EXAMPLE 13

2.48 g. (0.005 mol.) of 7-amino-3-[[(1-methyl-1H-tetrazol-5-yl)thio]methyl]-8-oxo-5-thia-1-azabicyclo[4.2.0]-oct-2-ene-2-carboxylic acid diphenylmethyl ester and 1.30 g. (0.006 mol.) of α-[(methoxymethyl)thio]benzeneacetic acid are dissolved in a mixture of 50 ml. of methylene chloride and 50 ml. of tetrahydrofuran, cooled to 0°–5° and a solution of 1.13 g. (0.055 mol.) of dicyclohexylcarbodiimide in 10 ml of tetrahydrofuran is added dropwise with stirring. This is stirred for 90 minutes at 0°–5° and 90 minutes at room temperature. It is then filtered and the filtrate is concentrated. The residue is taken up with ethyl acetate, washed with sodium bicarbonate solution and with water, dried with magnesium sulfate and concentrated. The syrup like residue solidifies upon treatment with petroleum ether. 2.8 g. of 7β-[[[(methoxymethyl)thio]phenylacetyl]amino]-3-[[(1-methyl-1H-tetrazol-5-yl)thio]methyl]-8-oxo-5-thia-1-azabicyclo[4.2.0]oct-2-ene-2-carboxylic acid diphenylmethyl ester are obtained, m.p. < 65° (dec.).

EXAMPLE 14

1.1 g. of the product of Example 13 are added to a mixture of 24 ml. of trifluoroacetic acid and 7 ml. of anisole at 0°–5°, stirred for 10 minutes and concentrated in vacuo. The residue is taken up in a little ethyl acetate, the acid is extracted with sodium bicarbonate solution, the aqueous phase is acidified and the precipitated acid is taken up with a mixture of ethyl acetate and tetrahydrofuran (3:1). It is washed with water, dried with magnesium sulfate and concentrated. The residual 7β-[[[(methoxymethyl)thio]phenylacetyl]amino-3-[[(1-methyl-1-H-tetrazol-5-yl)thio]methyl]-8-oxo-5-thia-1-azabicyclo[4.2.0]oct-2-ene-2-carboxylic acid crystallizes upon trituration with petroleum ether, yield 0.36 g.

EXAMPLE 15

0.32 g. (0.0006 mol.) of the product of Example 14 is dissolved in 10 ml. of methanol, an equivalent amount of a 0.1N sodium bicarbonate solution is added and the methanol is then evaporated in vacuo. The residual aqueous solution is filtered and freeze dried. The yield of 7β-[[[(methoxymethyl)thio]phenyacetyl]amino-3-[[(1-methyl-1 H-tetrazol-5-yl)thio]methyl-8-oxo-5-thia-1-azabicyclo[4.2.0]oct-2-ene-2-carboxylic acid, sodium salt is 0.3 g., decomposes < 80°.

EXAMPLES 16–47

The products below are obtained by reacting the acid

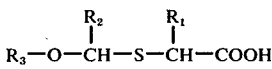

with the diphenylmethyl ester or other derivative of one of the following according to the procedure of Example 13 and then following with the procedure of Example 14. Salts are produced by continuing with the procedure of Example 15.

3-[[(5-methyl-1,3,4-thiadiazolyl-2-yl)thio]-methyl]-7-amino-8-oxo-5-thia-1-azabicyclo[4.2.0]oct-2-ene-2-carboxylic acid 3-[[(1-methyl-1H-tetrazol-5-yl)thio]methyl]-7-ACA
3-[[(1,3,4-oxadiazol-2-yl)thio]methyl]-7-ACA
3-[[(5-ethyl-1,3,4-oxadiazol-2-yl)thio]methyl]-7-ACA
3-[[(1,2,3,4-tetrazol-5-yl)thio]methyl]-7-ACA
3-[[(1-ethyl-1H-tetrazol-5-yl)thio]methyl]-7-ACA
3-[[(3-methyl-1,2,4-thiadiazol-5-yl)thio]methyl]-7-ACA
3-[[(1,3,4-thiadiazol-5-yl)thio]methyl]-7-ACA
3-[[(3-butyl-1,2,4-thiadiazol-5-yl)thio]methyl-7-ACA
3-[[(1,2,3,4-thiatriazol-5-yl)thio-]methyl]-7-ACA
3-[[(5-methyl-1,3,4oxadiazol-2-yl)thio]methyl-7-ACA
3-[[(1,2,4-thiadiazol-5-yl)thio]methyl]-7-ACA
3-[[(4-pyridinyl-N-oxide)thio]methyl]-7-ACA
3-[[(2-pyridinyl-N-oxide)thio]methyl]-7-ACA
3-[[(3-pyridinyl-N-oxide)thio]methyl]-7-ACA
3-[[(1,2,3-triazol-5yl)thio]methyl]-7-ACA
3-[[(1-methyl-1,2,3-triazol-5-yl)thio]methyl]-7-ACA

EXAMPLE 16   7β-[[[[(n-butyloxy)methyl]thio]-2-phenylacetyl]-amino]-3-[[(1,3,4-oxadiazol-2-yl)thio]methyl]-8-oxo-5-thia-1-azabicyclo[4.2.0]oct-2-ene-2-carboxylic acid 17   7β-[[[[(ethoxy)methyl]thio]-2-(2-furyl)acetyl]-amino]-3-[[(5-ethyl-1,3,4-oxadiazol-2-yl)thio]methyl]-8-oxo-5-thia-1-azabicyclo[4.2.0]oct-2-ene-2-carboxylic acid 18   7β-[[[[(ethoxy)methyl]thio]-2-(2-thienyl)acetyl]-amino]-3-[[(1,2,3,4-thiatriazol-5-yl)thio]methyl]-8-oxo-5-thia-1-azabicyclo[4.2.0]oct-2-ene-2-carboxylic acid 19   7β-[[[[2-(phenylmethoxy)methyl]thio]-2-phenylacetyl]-amino]-3-[[(1,2,3,4-tetrazol-5-yl)thio]methyl]-8-oxo-5-thia-1-azabicyclo[4.2.0]oct-2-ene-2-carboxylic acid 20   7β-[[[[(propoxy)methyl]thio]-2-phenylacetyl]-amino]-3-[[(1,2,4-thiadiazol-5-yl)thio]methyl]-8-oxo-5-thia-1-azabicyclo[4.2.0]oct-2-ene-2-carboxylic acid 21   7β-[[[[(2-phenylethoxy)methyl]thio]acetyl]-amino]-3-[[(1,2,4-thiadiazol-5-yl)thio]methyl]-8-oxo-5-thia-1-azabicyclo[4.2.0]oct-2-ene-2-carboxylic acid 22   7β-[[[(methoxy)methyl]thio]-2-phenylacetyl]-amino]-3-[[(3-butyl-1,2,4-thiadiazol-5-yl)thiomethyl]-8-oxo-5-thia-1-azabicyclo[4.2.0]oct-2-ene-2-carboxylic acid 23   7β-[2-[[(methoxy)methyl]thio]butyramido]-3-[[(1,2,3,4-tetrazol-5-yl)thio]methyl]-8-oxo-5-thia-1-azabicyclo[4.2.0]oct-2-2-ene-2-carboxylic acid 24   7β-[2-[[(phenylmethoxy)methyl]thio]propionamido]-3-[[(1-methyl-1H-tetrazol-5-yl)thio]-methyl]-8-oxo-5-thia-1-azabicyclo[4.2.0]oct-2-ene-2-carboxylic acid 25   7β-[[[[(methoxy)methyl]thio]-2-phenylacetyl]-amino]-3-[[(5-methyl-1,3,4-oxadiazol-2-yl)thio]-methyl]-8-oxo-5-thia-1-azabicyclo[4.2.0]oct-2-ene-2-carboxylic acid and potassium salt 26   7β-[[[(methoxy)methyl]thio]acetyl]amino]-3-[[1-ethyl-1H-tetrazol-5-yl)thio]methyl-8-oxo-5-thia-1-azabicyclo[4.2.0]oct-2-ene-2-carboxylic acid 27   7β-[[[[(methoxy)methyl]thio]-2-phenylacetyl]-amino]-3-[[(1-ethyl-1H-tetrazol-5-yl)thio]methyl]-8-oxo-5-thia-1-azabicyclo[4.2.0]oct-2-ene-2-carboxylic acid 28  7β-[[[[(ethoxy)methyl]thio]-2-phenylacetyl]amino-]-3-[[(5-methyl-1,3,4-thiadiazol-2-yl)thio]methyl]-8-oxo-5-thia-1-azabicyclo[4.2.0]oct-2-ene-2-carboxylic acid and ethyl ester.

29  7β-[[[[(ethoxy)methyl]thio]-2-(2-furyl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid and potassium salt 30  7β-[[[[(propoxy)methyl]thio]-2-(2-thienyl)acetyl]amino]-3-[[(1,3,4-oxadiazol-2-yl)thio]methyl]-8-oxo-5-thia-1-azabicyclo[4.2.0]oct-2-ene-2-carboxylic acid and sodium salt 31  7β-[[[[(phenyloxy)methyl]thio]acetyl]amino]-3-[[(5-ethyl-1,3,4-oxadiazol-2-yl)thio]methyl]-8-oxo-5-thia-1-azabicyclo[4.2.0]oct-2-ene-2-carboxylic acid 32  7β-[[[[(n-butyloxy)methyl]thio]acetyl]amino]-3-[[(1,2,3,4-tetrazol-5-yl)thio]methyl]-8-oxo-5-thia-1-azabicyclo[4.2.0]oct-2-ene-2-carboxylic acid 33  7β-[[[[(phenylmethyloxy)methyl]thio]-2-(3-furyl)acetyl]amino]-3-[[(1,2,4-thiadiazol-3-yl)thio]methyl]-8-oxo-5-thia-1-azabicyclo[4.2.0]oct-2-ene-2-carboxylic acid pivaloyloxymethyl ester 34  7β-[[[[(methoxy)methyl]thio]-2-(2-furyl)acetyl]amino]-3-[[(1,2,3,4-thiatriazol-5-yl)thio]methyl]-8-oxo-5-thia-1-azabicyclo[4.2.0]oct-2-ene-2-carboxylic acid trimethylsilyl ester 35  7β-[[[[(methoxy)methyl]thio]-2-(2-thienyl)acetyl]amino]-3-[[(1,3,4-oxadiazol-2-yl)thio]methyl]-8-oxo-5-thia-1-azabicyclo[4.2.0]oct-2-ene-2-carboxylic acid phenylmethyl ester 36  7β-[[[[(ethoxy)methyl]thio]-2-phenylacetyl]amino]-3-[[(2-pyridinyl-N-oxide)thio]methyl]-8-oxo-5-thia-1-azabicyclo[4.2.0]oct-2-ene-2-carboxylic acid 37  7β-[[[[(phenylmethyloxy)methyl]thio]-2-phenylacetyl]-amino]-3-[[(2-pyridinyl-N-oxide)-thio]methyl]-8-oxo-5-thia-1-azabicyclo[4.2.0]oct-2-ene-2-carboxylic acid pivaloyloxymethyl ester 38  7β-[[[[(methoxy)methyl]thio]acetyl]amino]-3-[[(4-pyridinyl-N-oxide)thio]methyl]-8-oxo-5-thia-1-azabicyclo[4.2.0]-oct-2-ene-2-carboxylic acid and potassium salt 39  7β-[[[[(methoxy)methyl]thio]-2-phenylacetyl]amino]-3-[[(5-methyl-1,3,4-thiadiazol-2-yl)thio]methyl]-8-oxo-5-thia-1-azabicyclo[4.2.0]oct-2-ene-2-carboxylic acid and sodium salt 40  7β-[[[[1-(methoxy)ethyl]thio]acetyl]amino]-3-[[(1-methyl-1H-tetrazol-5-yl)thio]methyl]-8-oxo-5-thia-1-azabicyclo[4.2.0oct-2-ene-2-carboxylic acid 41  7β-[[[[1-(phenyloxy)propyl]thio]-2-phenylacetyl]amino]-3-[[(1-methyl-1H-tetrazol-5-yl)thio]methyl]-8-oxo-5-thia-1-azabicyclo[4.2.-0]oct-2-ene-2-carboxylic acid 1-acetoxyethyl ester 42  7β-[[[[(methoxy)methyl]thio]-2-phenylacetyl]amino]-3-[[(1,2,3-triazol-5-yl)thio]methyl]-8-oxo-5-thia-1-azabicyclo[4.2.0]oct-2-ene-2-carboxylic acid and sodium salt.

43  7β-[[[[(phenylmethyloxy)methyl]thio]acetyl]amino]-3-[[(1-methyl-1,2,3-triazol-5-yl)thio]methyl]-8-oxo-5-thia-1-azabicyclo[4.2.0-oct-2-ene-2-carboxylic acid 44  7β-[2-[[(phenoxy)methyl]thio]propionamido]-3-[[(1-ethyl-1,2,3-triazol-5-yl)thio]methyl]-8-oxo-5-thia-1-azabicyclo[4.2.0]oct-2-ene-2-carboxylic acid 45  7β-[[[(methoxy)methyl]thio]acetylamino]-3-[[(5-methyl-1,3,4-thiadiazol-2-yl)thio]methyl]-8-oxo-5-thia-1-azabicyclo[4.2.0]oct-2-ene-2-carboxylic acid and sodium salt 46  7β-[[[(methoxy)methyl]thio]acetylamino]-3-[[(3-methyl-1,2,4-thiadiazol-5-yl)thio]methyl]-8-oxo-5-thia-1-azabicyclo[4.2.0]oct-2-ene-2-carboxylic acid and sodium salt 47  7β-[[[[(methoxy)methyl]thio]-2-phenylacetyl]amino]-[[(3-methyl-1,2,4-thiadiazol-5-yl)thio]-methyl]-8-oxo-5-thia-1-azabicyclo[4.2.0]-oct-2-ene-2-carboxylic acid and potassium salt

What is claimed is:

1. A compound of the formula

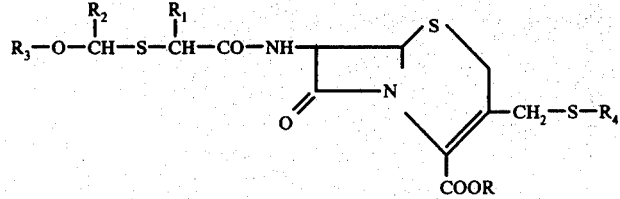

wherein R is hydrogen, lower alkyl, phenyl-lower alkyl, diphenyl-lower alkyl, tri(lower alkyl)silyl, alkali metal, alkaline earth metal, (lower alkyl)amine or

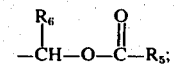

$R_1$ is hydrogen, lower alkyl, phenyl, thienyl or furyl; $R_2$ and $R_6$ each is hydrogen or lower alkyl; $R_3$ and $R_5$ each is lower alkyl, phenyl or phenyl-lower alkyl; $R_4$ is oxadiazol yl, thiadiazol yl, triazol yl, thiatriazol yl, tetrazol yl, 1-oxopyridin yl and their lower alkyl derivatives; said lower alkyl groups having 1 to 8 carbon atoms.

2. A compound as in claim 1 wherein $R_1$ is phenyl.
3. A compound as in claim 1 wherein $R_1$ is hydrogen.
4. A compound as in claim 1 wherein R is hydrogen, alkali metal, diphenylmethyl or

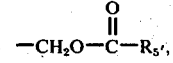

$R_1$ is hydrogen, lower alkyl, phenyl or thienyl; $R_2$ and $R_6$ each is hydrogen or lower alkyl; and $R_4$ is thiadiazol yl, (lower alkyl)thiadiazol yl, tetrazol yl or (lower alkyl)tetrazol yl.

5. A compound as in claim 1 wherein R and $R_2$ each is hydrogen, $R_1$ is phenyl and $R_3$ is lower alkyl.

6. A compound as in claim 1 wherein R is hydrogen or alkali metal, $R_2$ is hydrogen, $R_1$ is phenyl, $R_3$ is lower alkyl and $R_4$ is (lower alkyl)tetrazolyl.

7. A compound as in claim 6 wherein each lower alkyl group is methyl and R is hydrogen.

8. A compound as in claim 7 wherein the methyltetrazolyl is the 1-methyl-1H-tetrazol-5-yl radical.

9. Alkali metal salt of the compound of claim 8.

10. A salt as in claim 9 wherein the alkali metal is sodium.

11. A compound as in claim 1 wherein R is hydrogen or alkali metal, $R_1$ is hydrogen or phenyl, $R_2$ is hydrogen, $R_3$ is lower alkyl and $R_4$ is (lower alkyl)thiadiazolyl.

12. A compound as in claim 1 wherein R, $R_1$ and $R_2$ each is hydrogen, $R_3$ is lower alkyl and $R_4$ is (lower alkyl)tetrazolyl.

13. A compound as in claim 12 wherein each lower alkyl group is methyl.

14. A compound as in claim 13 wherein the (lower alkyl)tetrazole is the 1-methyl-1H-tetrazol-5-yl group.

15. Alkali metal salt of the compound of claim 14.

16. A salt as in claim 15 wherein the alkali metal is sodium.

* * * * *

UNITED STATES PATENT AND TRADEMARK OFFICE
CERTIFICATE OF CORRECTION

PATENT NO. : 3,989,696
DATED : November 2, 1976
INVENTOR(S) : Hermann Breuer et al.

It is certified that error appears in the above-identified patent and that said Letters Patent are hereby corrected as shown below:

In the Abstract, second line after the second formula after $R_5$ insert -- each --.

Column 1, line 39, insert the following structures --

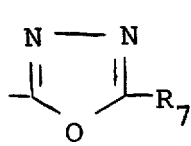 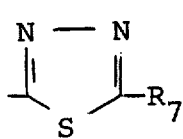 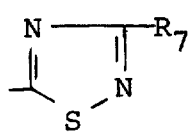 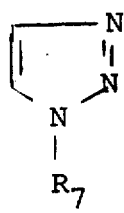

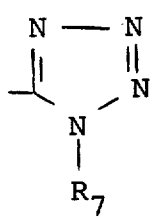 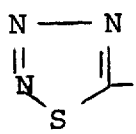 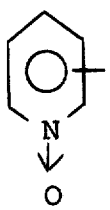

Column 8, line 13, after "4" should be inserted a hyphen.
Column 9, line 64, after "0" should be inserted -- ] --.

Signed and Sealed this second Day of August 1977

[SEAL]

Attest:

RUTH C. MASON
Attesting Officer

C. MARSHALL DANN
Commissioner of Patents and Trademarks